(12) United States Patent
Pawliszyn

(10) Patent No.: US 7,479,390 B2
(45) Date of Patent: Jan. 20, 2009

(54) DEVICE AND METHOD FOR MICRO SORBENT EXTRACTION AND DESORPTION

(76) Inventor: Janusz B. Pawliszyn, 383 Dunvegan Drive, Waterloo, Ontario (CA) N2K 1W7

( * ) Notice: Subject to any disclaimer, the term of this patent is extended or adjusted under 35 U.S.C. 154(b) by 888 days.

(21) Appl. No.: 10/496,516

(22) PCT Filed: Nov. 26, 2002

(86) PCT No.: PCT/CA02/01811

§ 371 (c)(1),
(2), (4) Date: May 21, 2004

(87) PCT Pub. No.: WO03/046517

PCT Pub. Date: May 6, 2003

(65) Prior Publication Data

US 2005/0014156 A1    Jan. 20, 2005

(51) Int. Cl.
*G01N 35/00* (2006.01)
*A61L 2/28* (2006.01)
(52) U.S. Cl. ............... 436/43; 436/139; 436/145; 436/106; 436/119; 436/161; 436/174; 436/178; 422/50; 422/119; 422/243; 422/142
(58) Field of Classification Search ............... None
See application file for complete search history.

(56) References Cited

U.S. PATENT DOCUMENTS 4,944,781 A * 7/1990 Ruggirello et al. ......... 73/23.41
4,980,294 A * 12/1990 Elias et al. ................. 436/21
5,483,843 A * 1/1996 Miller et al. ............. 73/864.23

(Continued)

FOREIGN PATENT DOCUMENTS

WO    WO 0120320    * 3/2001

(Continued)

OTHER PUBLICATIONS

Supelco Bulletin 879A, GC and HPLC phases and packings for US Pharmacopoeia methods, 1998.*

(Continued)

*Primary Examiner*—Jill Warden
*Assistant Examiner*—Timothy G Kingan
(74) *Attorney, Agent, or Firm*—Andrew D. Sojonky; Borden Ladner Gervais LLP

(57) ABSTRACT

This invention relates to a micro cartridge and to a method of using the micro cartridge to sample and extract components of interest from a gas or a liquid. The cartridge contains a sorbent and has passages through which a pressure drop can be created to permit access between the gas or liquid and the sorbent. The micro cartridge is elongated and has one pointed end to fit into the injection port of a suitable analysis instrument where the components of interest are desorbed. The cartridge has two ends that are covered by removable closures and preferably has a diameter of less than 1 millimeter. The cartridge can be used with micro machine components and components made using nano technology.

20 Claims, 17 Drawing Sheets

U.S. PATENT DOCUMENTS 5,720,798 A * 2/1998 Nickerson et al. ............. 96/102
6,042,787 A * 3/2000 Pawliszyn .................... 422/69
6,093,371 A * 7/2000 Wilson ........................ 422/89
6,177,008 B1 * 1/2001 Treiber et al. ............ 210/198.2

FOREIGN PATENT DOCUMENTS

WO            02086488 A1    10/2002

OTHER PUBLICATIONS

Pellizzari, E.D., Carpenter, B.H. and J.E.Bunch, "Collection and analysis of trace organic vapor pollutants in ambient atmospheres", Environmental Science & Technology 9(6):556-560, 1975.*

Raschdorf, F., "Rapid measurements in the ppm and ppb region", Chimia 32(12): 478-483, 1978.*

Sigman, M.E., Ma, C-Y. and R.H. Ilger, "Performance evaluation of an in-jection port thermal desorption/gas chromatographic/megative ion chemical ionization mass spectrometric method for trace explosive vapor analysis", Anal. Chem. 73: 792-798, Feb. 15, 2001.*

* cited by examiner

DEVICE AND METHOD FOR MICRO SORBENT EXTRACTION AND DESORPTION

BACKGROUND OF THE INVENTION

1. Field of Invention

This invention relates to a device for sampling and extracting components of interest from fluid containing particulates into a method of operation thereof. More particularly, this invention relates to a micro cartridge containing a sorbent where outside access to the sorbent can be open or closed and the micro cartridge is sized and shaped to fit into an injection port of a suitable analysis instrument

2. Description of the Prior Art

It is known to have a needle trap whereby a particulate matter can be collected and directly desorbed into an analytical instrument as described in U.S. patent application Ser. No. 09/771,666. The needle has two ends with an extraction trap located between the ends. Both ends of the needle are open and the needle is connected to syringe having a barrel and plunger. The barrel and plunger are used to cause air to flow through the trap by operating the plunger. An inexpensive hypodermic needle and syringe can be used to construct and operate the needle trap device.

While the needle trap works generally well, the packing or sorbent forming the trap sometimes protrudes or slips completely out of the end of the needle. Also, while the needle trap is portable, it is difficult to use in the field where the analytical instrument is some distance away from the location where the sample is taken. The needle is relatively difficult to make completely airtight after a sample has been collected and therefore cannot be easily protected from contamination after a sample has been taken and before the sample is desorbed into an analytical instrument. Since packing the needle is a time consuming process, the needle trap cannot reasonably be considered to be a disposable item. Also, as with any needle, it must be handled extremely carefully by a user and is not particularly suited to passive collection of samples. Further, the needle is relatively bulky. Still further, sometimes, the packing in the needle at an end away from the barrel and plunger will tend to clog with sample matrix, thereby interfering with the flow of sample and therefore making the sampling and extraction process inaccurate.

SUMMARY OF THE INVENTION

It is an object of the present invention to provide a micro cartridge that can be made of stainless steel, fused silica or other suitable material, the cartridge having two closed ends and containing a sorbent It is a further object of the present invention to provide a device that can be used for sampling and extracting components of interest in a safe, inexpensive and accurate manner whether the device is used for active sampling or passive sampling. It is a further object of the present invention to provide a device that can be used for sampling and extracting components of interest and where the device can be inserted directly into an injection port of an analysis instrument. It is a further object of the present invention to provide a micro device that can be used for sampling and extracting components of interests form small and living objects. It is a further object of the present invention to provide a micro device that can be inserted directly into a micromachined analysis instrument.

It is a further object of the present invention to provide a micro cartridge that can be used for sampling and extraction where the device can be contained in an airtight housing for transport purposes.

A device for sampling and extracting components of interest from fluid has an elongated micro cartridge. The cartridge contains a sorbent and has passages therein through which a pressure drop can be created within the cartridge to permit access between the fluid and the sorbent. The micro cartridge is sized and shaped to fit into an injection port of a suitable analysis instrument where the components of interest can be desorbed.

A method of using a device for sampling and extracting components of interest from fluid, the device having an elongated micro cartridge containing a sorbent and having passages therein through which a pressure drop can be created within the cartridge to permit access between the fluid and the sorbent The method comprises exposing the micro cartridge and sorbent to a fluid, inserting the cartridge into an injection port of a suitable analysis instrument and desorbing the components of interest from said cartridge.

Preferably, after use, the cartridge is disposed of.

DESCRIPTION OF A PREFERRED EMBODIMENT

Figure 1:
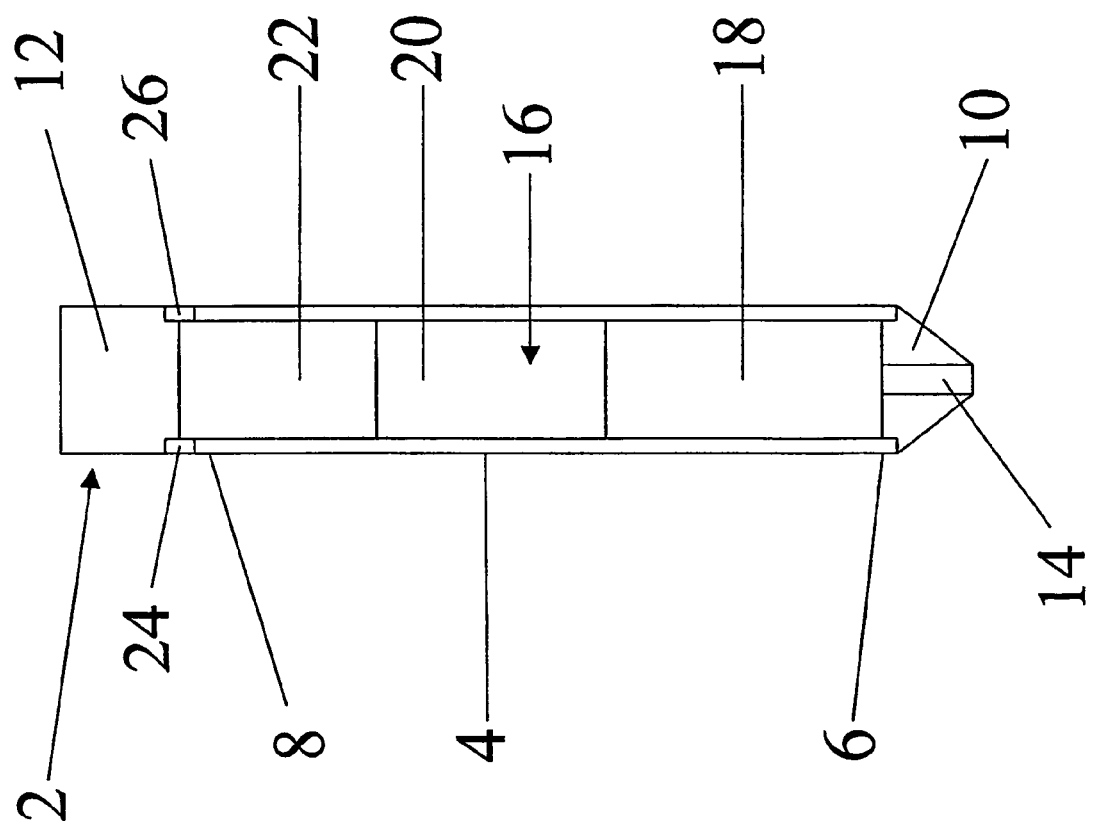
FIG. 1 is a schematic side view of a micro cartridge containing a segmented sorbent.

In the drawings, in FIG. 1, there is shown a micro cartridge 2 having a tubular member 4 with two ends 6, 8. The ends 6, 8 are closed with removable closures 10, 12 respectively. The closure 10 converges outwardly and has a centrally located first passage 14 therein. The closure 12 has a generally rectangular cross sectional shape and is located in the end 8. The cartridge 2 is filled with a sorbent 16 having three different segments 18, 20, 22. A second passage 24 and a third passage 26 is located in the tubular member 4 at the end 8. The micro cartridge 2 is preferably made from metal, glass or other suitably inert material. Preferably, the metal is stainless steel or more preferably, silco steel. The micro cartridge can also be manufactured from deactivated metal and fused silica. The micro cartridge can be manufactured using micromachined technology and/or nano technology materials and components. The sorbent materials can be in form of small particles larger then the passage 14 to prevent loss of sorbent and contamination of sample or analytical instrument. The sorbent can also be produced by direct in-cartridge in-situ polymerization, for example through the sol-gel process of appropriate monomers like tetramethoxysilane [M. Motokawa, at al. J. Chromatogr. A, 961, 53-63 (2002)]. This process results in a highly porous monolithic sorbent inside the cartridge facilitating low resistance to flow of the sample matrix during extraction and carrier fluid during desorption into analytical. Since it is a monolith it will more likely remain in the cartridge. To prevent loss of sorbent, the sorbent can be bound to the surface of the cartridge by using appropriate polymerization process which can be obtained in-situ polymerization. The sorbent can contain derivatization reagent to react with analytes. The reagent can perform various functions, including converting unstable analytes to more stable analogs, enhancement of extraction and detection. For example, when analyzing for unstable formaldehyde, pentaflorohydrozamine can be used to obtain appropriate stable oxime. The formaldehyde is then quantified as oxime [J. Koziel, J. Noah and J. Pawliszyn Environmental Science & Technology 35, 1481-1486 (2001)]. The derivatization can also be performed following the extraction by introducing appropriate reagent to the micro cartridge after the extraction has been completed.

Figure 2:
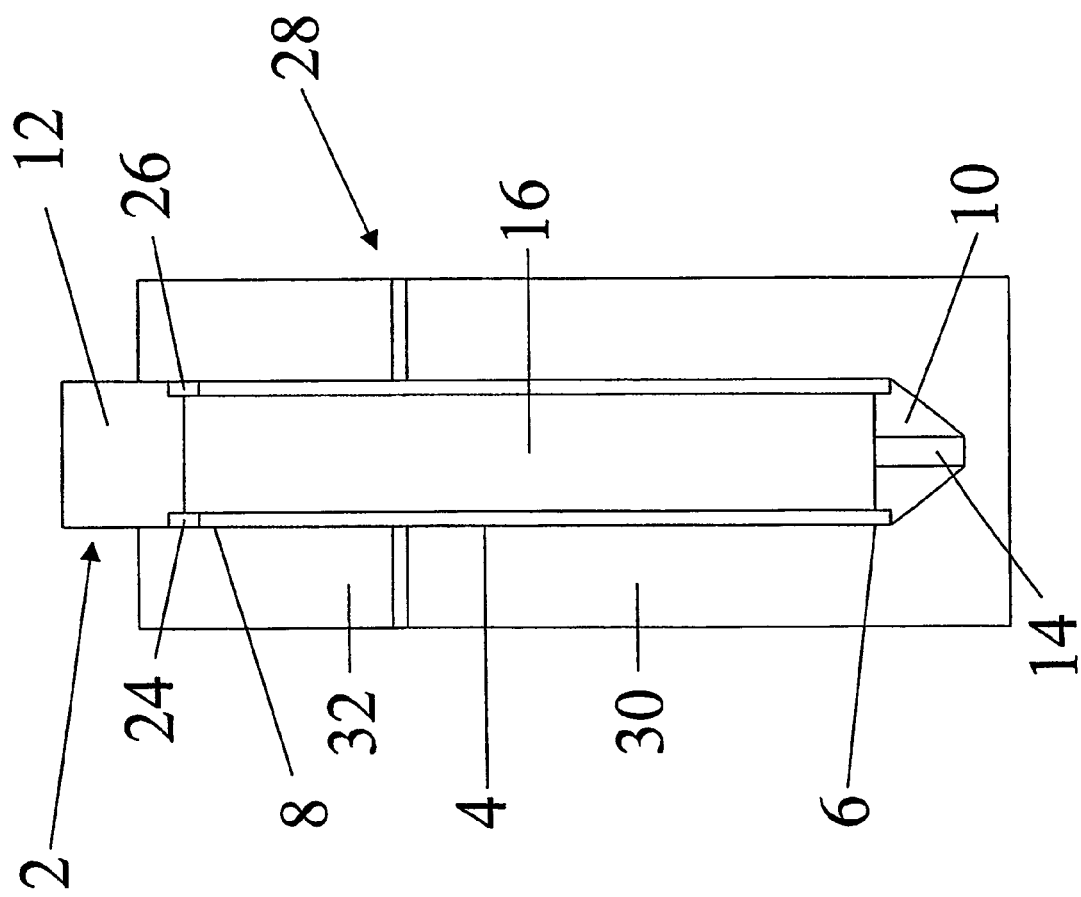
FIG. 2 is a schematic side view of the micro cartridge being enclosed in a sealed housing having two parts.

In FIG. 2, the micro cartridge 2 is located within a sealed housing 28 having two removable parts 30, 32. The housing 28 closes off all of the passages 24, 26 and 14. The same reference numerals are used in FIGS. 2, 3 and 4 for the cartridge 2 as those used in FIG. 1 for those components that are identical.

Figure 3:
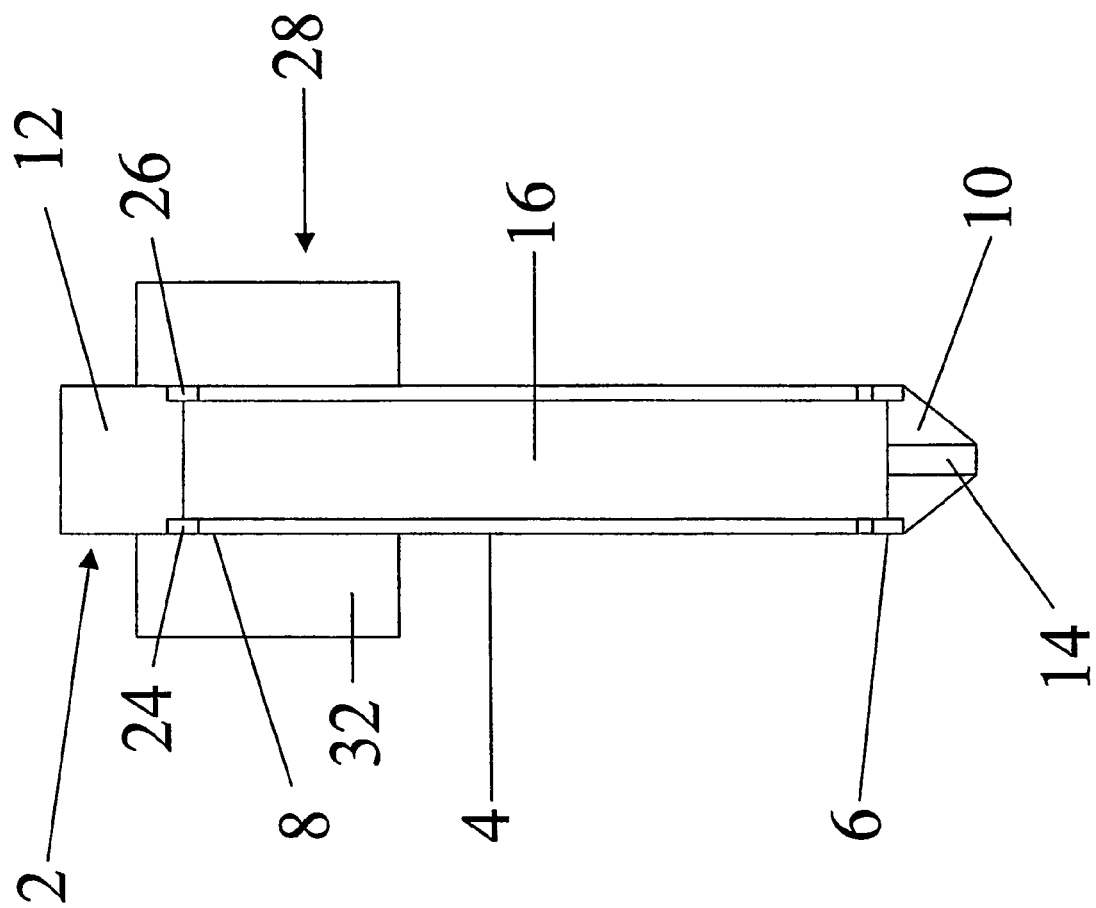
FIG. 3 is a schematic side view of a micro cartridge where part of the housing has been removed.

In FIG. 3, there is shown a sectional side view of the cartridge 2 shown in FIG. 2, the cartridge being located in the part 32 of the housing 28. The other part 30 of the housing has been removed and is not shown in FIG. 3. The part 32 closes off the second passage 24 and the third passage 26. The embodiment shown in FIG. 3 with the part 32 of the housing 28 removed can be used for passive sampling.

Figure 4:
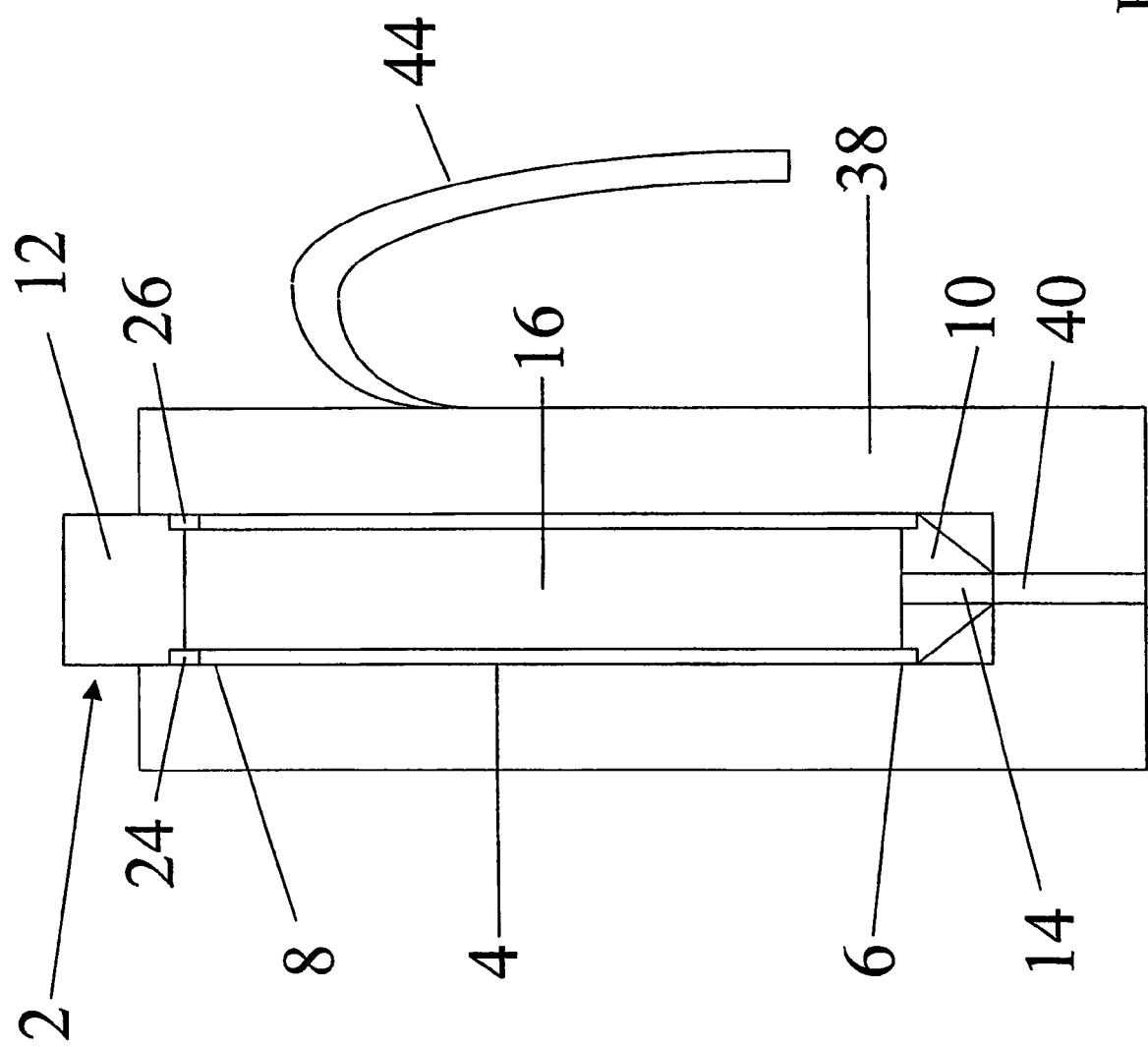
FIG. 4 is a schematic side view of a cartridge located within a housing wherein the housing has an opening that can be closed off.

In FIG. 4, there is shown a sectional side view of a further embodiment of the invention in which the cartridge 2 is located within a housing 38. The housing 38 has an opening 40 therein to connect with passage 14. The housing 38 has a clip 44 thereon so that the housing 38 including the cartridge 2 can be clipped on to a particular location or clipped on to a pocket of a user for passive sampling. When the sampling is completed, the opening 40 can be plugged with plugs (not shown). The housing 38 could have more than one opening 40 corresponding to other passages of the micro cartridge 2.

Figure 5:
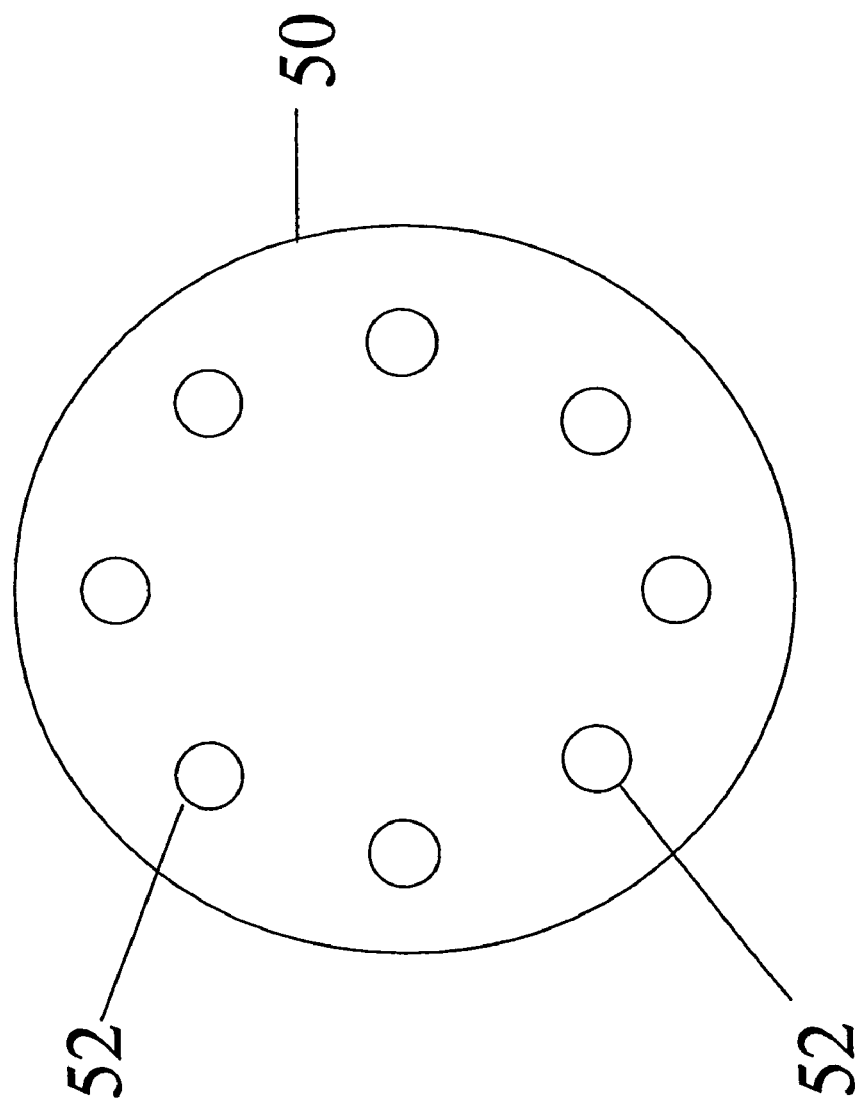
FIG. 5 is a top view of a carousel for an auto sampler where the carousel contains receptacles for cartridges.

In FIG. 5, there is shown a top view of a carousel 50 as an example of multi cartridge holder having a plurality of receptors 52 for receiving micro cartridges (not shown).

Figure 6:
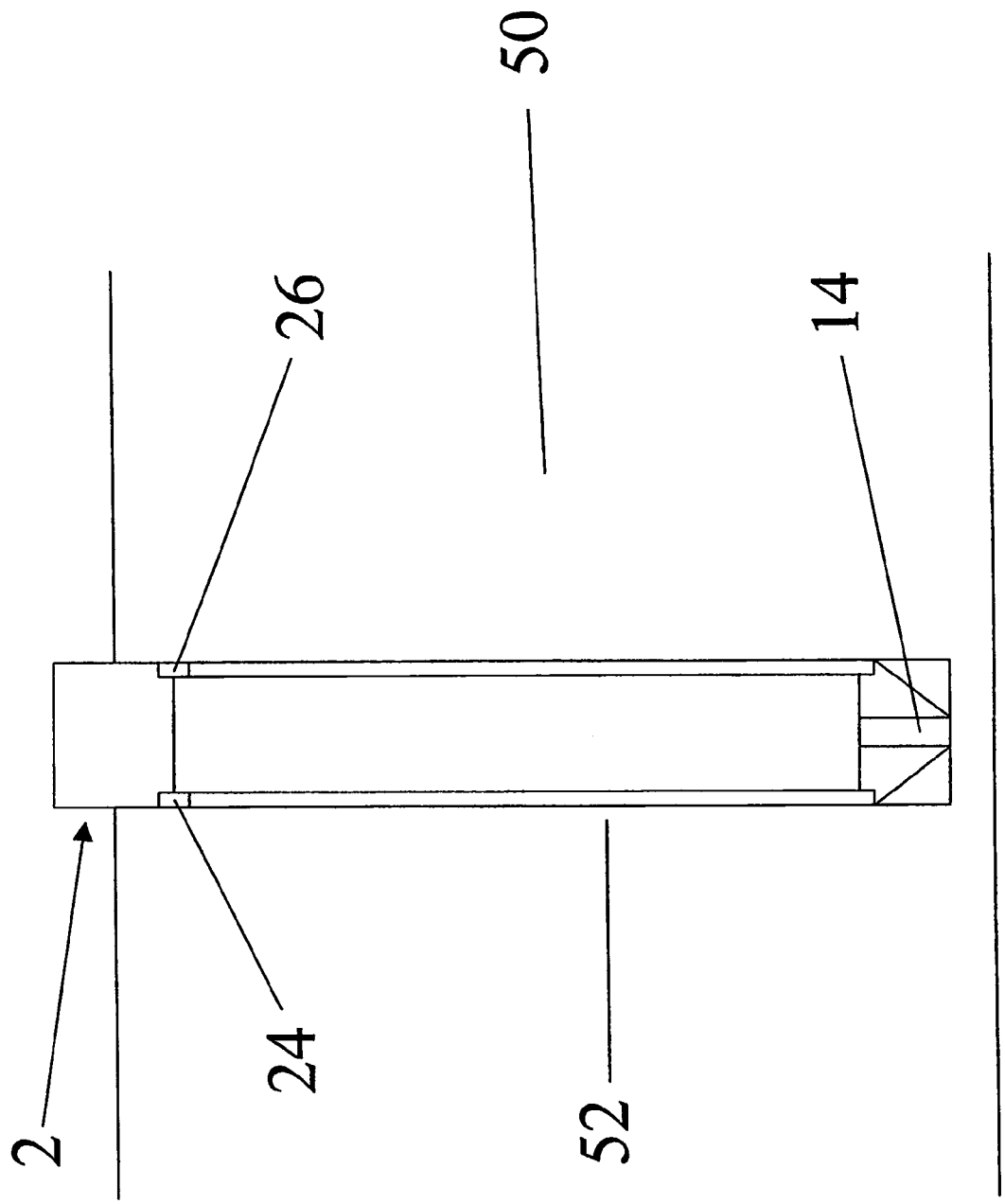
FIG. 6 is a schematic side view of one receptacle containing micro cartridge in part of a carousel.

In FIG. 6, there is shown a partial sectional side view of one receptor 52 in the carousel 50 with a cartridge 2 inserted therein. It can be seen that the passages 24, 26 and 14 of the cartridge 2 are sealed off when the cartridge is located in the receptor.

Figure 7:
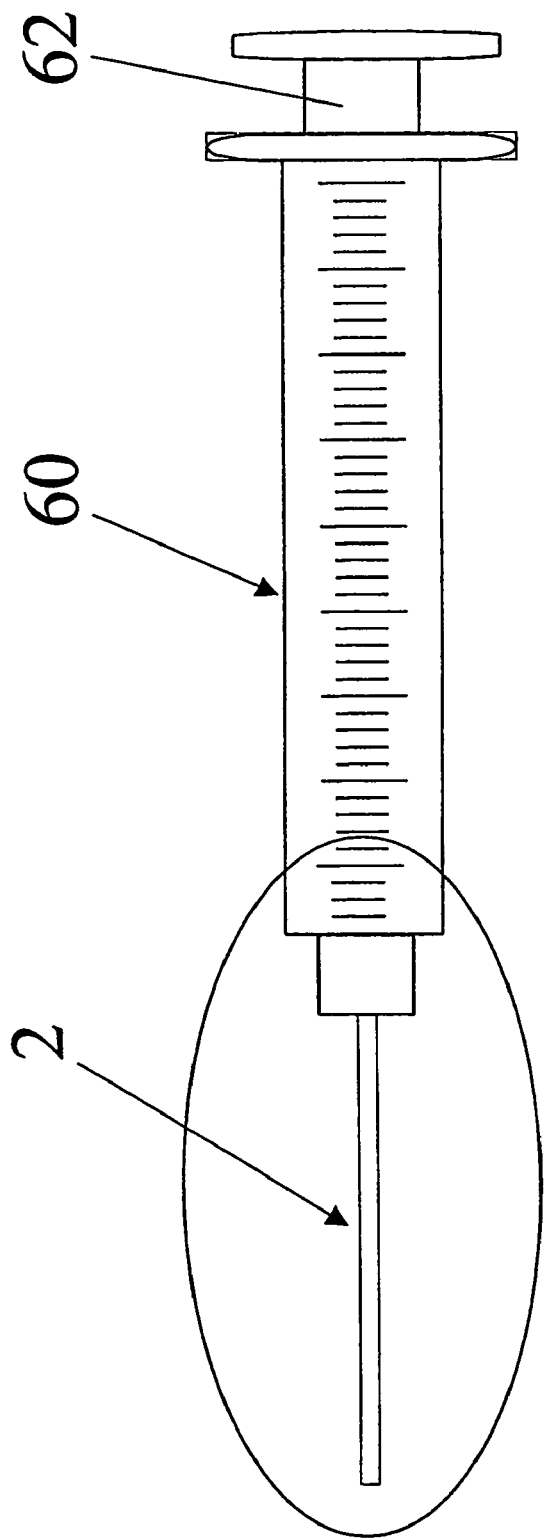
FIG. 7 is a schematic side view of the micro cartridge affixed to a barrel and plunger.
Figure 8:
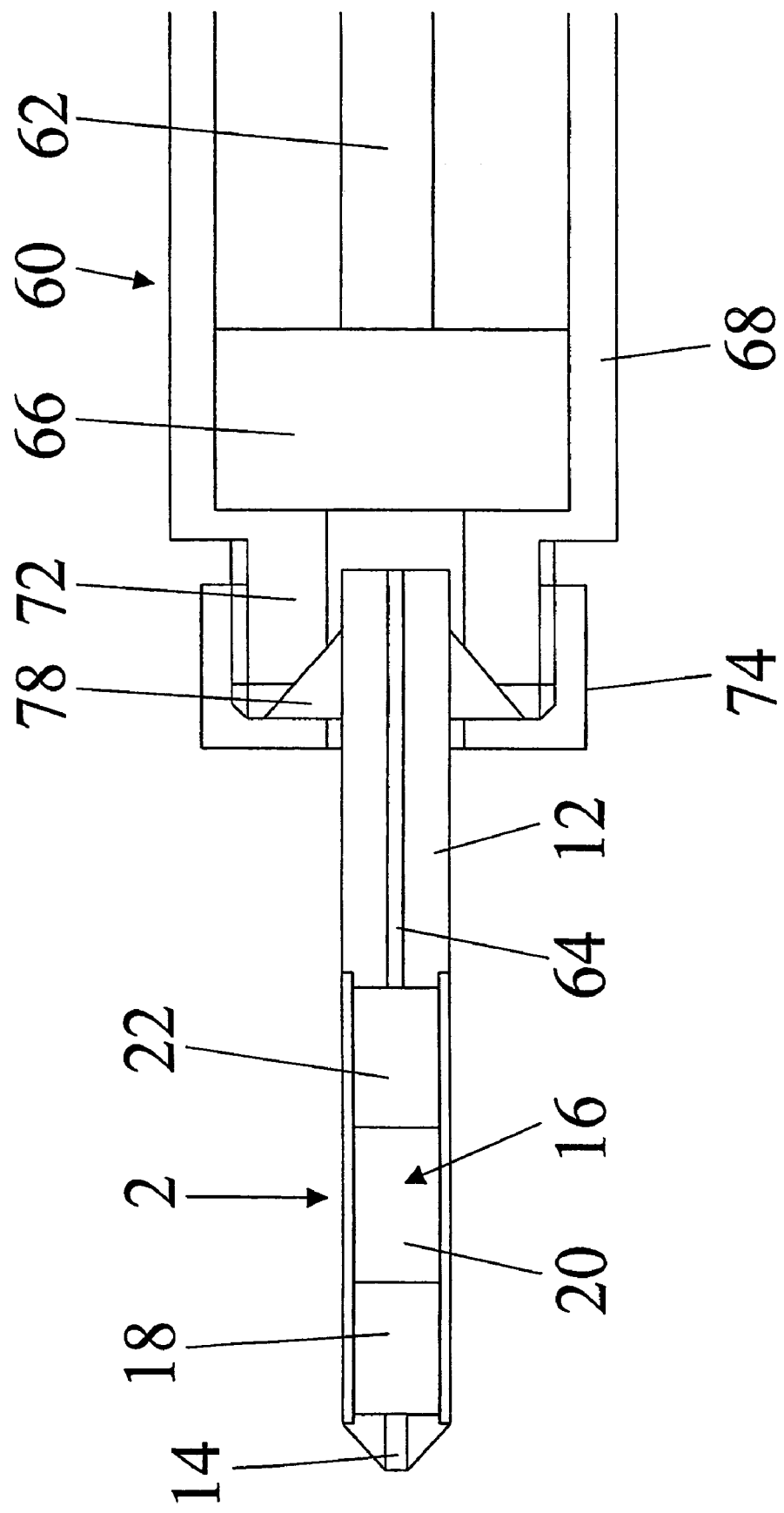
FIG. 8 is a partial schematic side view of a micro cartridge containing a segmented sorbent.

FIGS. 7 and 8 illustrate the operation of the micro cartridge 2 with a syringe 60. By withdrawing the plunger 62 during sampling and extraction, a well-defined volume of the sample can be drawn through the cartridge by the plunger 62. FIG. 8 illustrates the modified embodiment of the invention where the closure 12 is a thick-walled tubing and openings 24 and 26 are not used. The sample fluid is drawn through the opening in tubing-closure 12. When the plunger 62 is being pushed in during the desorption step the desorption fluid contained in a syringe barrel 68 is delivered to the sorbent 16 through the opening 64 in closure 12 and transports desorbed analytes into the analytical instrument. There is shown in FIG. 8 a partial schematic side view of a micro cartridge 2 containing a segmented sorbent with segments 18, 20, 22 mounted into a syringe via closure 12 with a help of a nut 74 and a ferrule 78. Syringe contains the threaded receptacle 72 for the nut 74. Using similar connections, the micro cartridge can be connected to pump or other device which can draw or pump sample fluid. The embodiment of invention showed on FIG. 1 can also be operated during sampling in a similar way by sealing the ferrule around tubing 4 rather then closure 12. In such arrangement, the fluid would be drawn via opening 24 and 26.

Figure 12:
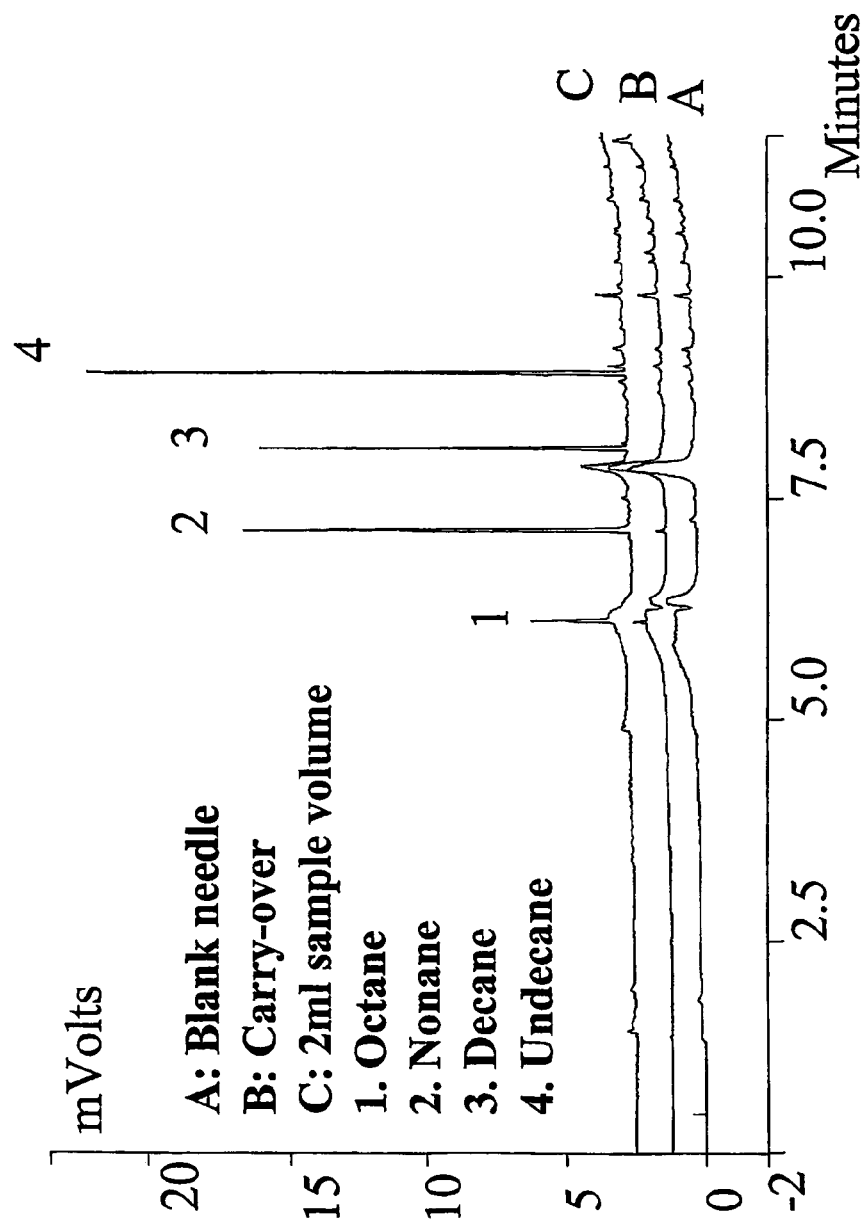
FIG. 12 is a graph of exhaustive extraction using micro cartridge.
Figure 13:
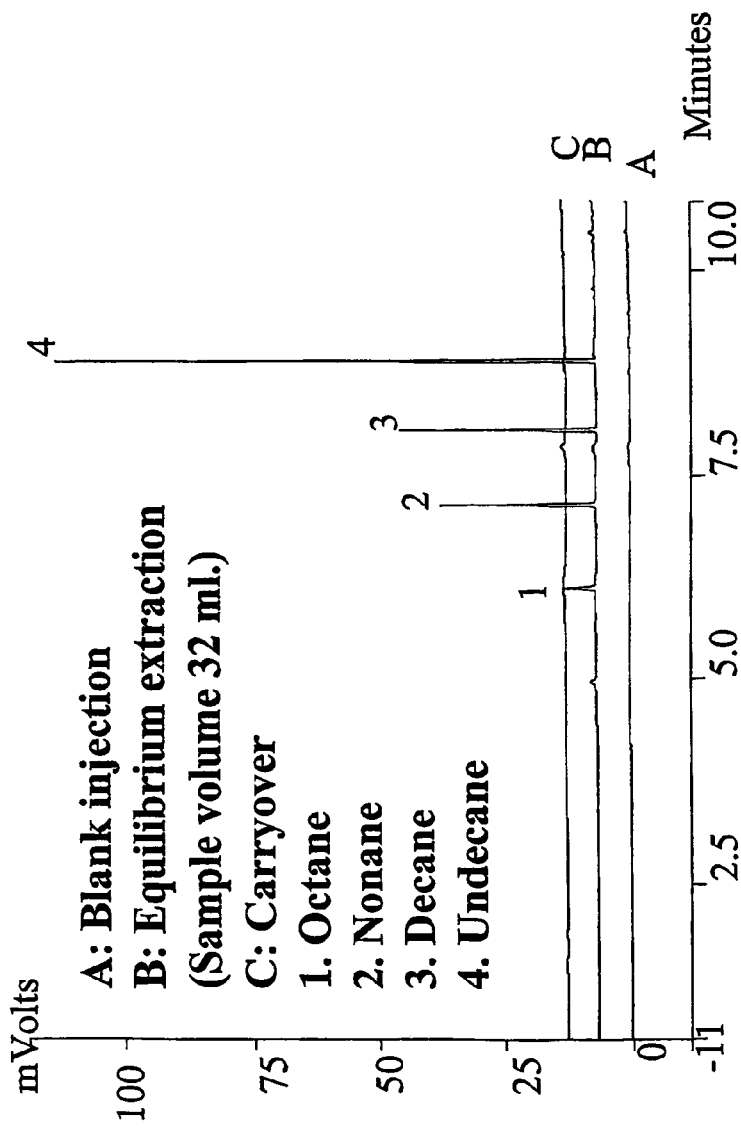
FIG. 13 is a graph of equilibrium extraction using micro cartridge.

Use of such micro cartridges in combination with a syringe allows for convenient sampling. The micro cartridge can be a needle, but is preferably not a micro cartridge. The device can be used as active sampler, by drawing the gas or liquid sample through the micro cartridge, for example, when using a gas tight syringe attached to the micro cartridge (FIG. 7). As FIG. 8 indicates, the preferred sorbent arrangement in the micro cartridge consists of several layers or segments 18, 20, 22 of sorbent. Weak sorbent 18 (for example: Poly(dimethylsiloxane) PDMS) is located closest to the cartridge opening, followed by medium strength sorbent 20 (for example: Polydivinylbezene polymer DVB) and strongly binding sorbent 22 such as activated carbon. This arrangement of sorbent facilitates efficient desorption since easily extracted components are trapped by the weakly binding sorbent 18, which is located closest to the exit. The flow of the desorption fluid is reversed in the desorption step compared to flow of the matrix in the extraction step and therefore this arrangement facilitates quantitative desorption. Active sampling can be performed, either in exhaustive mode by trapping all analytes present in the relatively small volume of a drawn air (FIG. 12 and Table 1), or, in microextaction mode when equilibrium is reached between air and the sorbing material after a substantially larger sample volume passes through the micro cartridge (FIG. 13 and Table 2). In exhaustive extraction, cooling of the micro cartridge would be beneficial since it allows quantitative trapping for larger volumes of samples.

TABLE 1

Exhaustive extraction with Micro Cartridge Device (MCD)

| item | Mass (ng) extracted 2 ml of sample | | | |
| --- | --- | --- | --- | --- |
| | Octane | Nonane | Decane | Undecane |
| Blank | 0.00 | 0.00 | 0.00 | 0.00 |
| Carry-over | 0.00 | 0.00 | 0.00 | 0.00 |
| Needle desorption | 0.31 | 1.22 | 0.97 | 1.34 |

TABLE 2

Equilibrium microextraction with Micro Cartridge Device (MCD)

| item | Mass (ng) extracted 32 ml sample | | | |
|---|---|---|---|---|
| | Octane | Nonane | Decane | Undecane |
| Expri. 1 | 0.98 | 2.33 | 2.62 | 7.12 |
| Expri. 2 | 0.68 | 2.48 | 2.89 | 7.24 |
| Expri. 3 | 0.71 | 2.33 | 2.90 | 7.22 |

Figure 9:
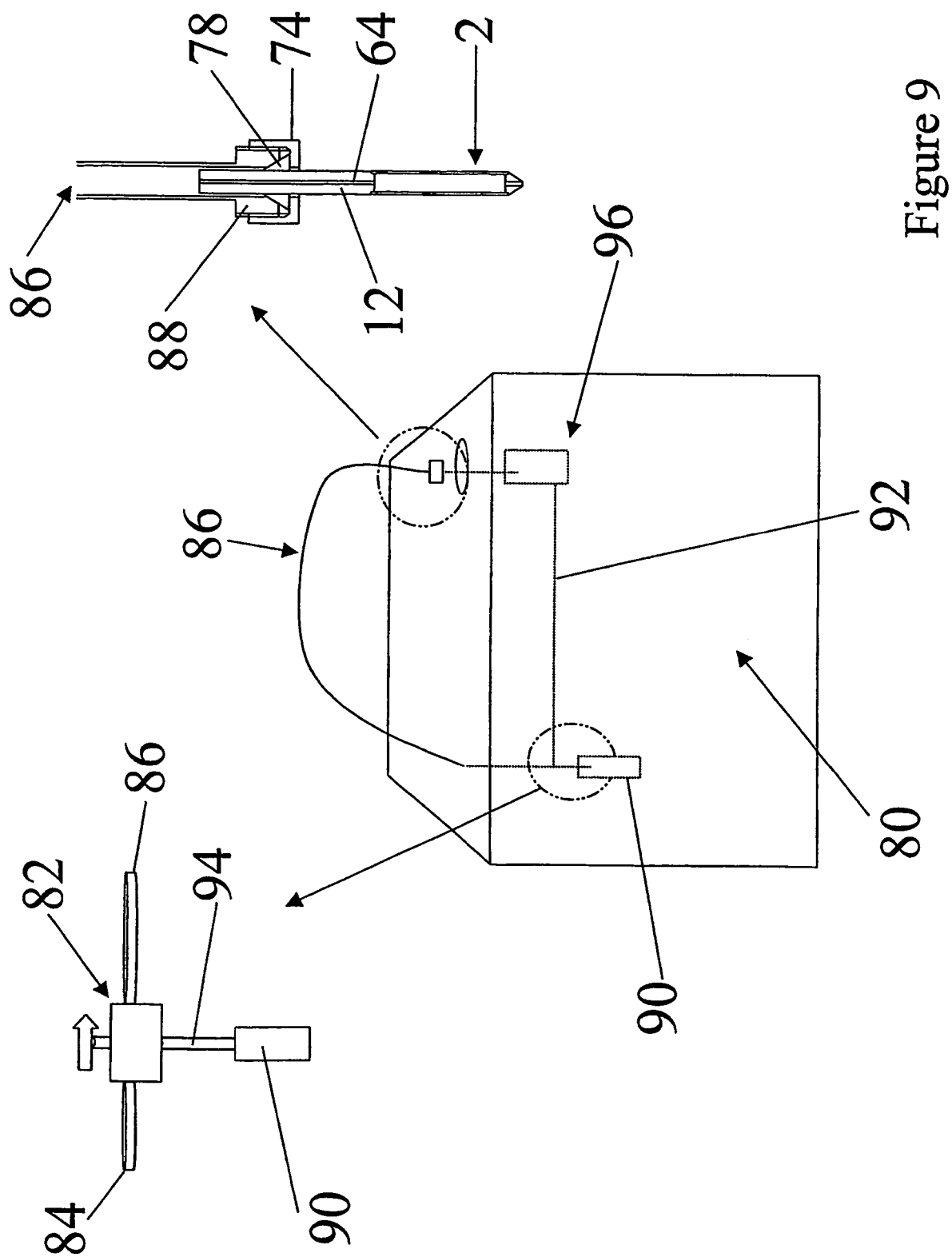
FIG. 9 is a side view of the micro cartridge device in the injector port of a gas chromatograph where carrier gas is diverted through the device during desorption using a valve.

The major disadvantages of using the syringe during desorption include introduction of the oxygen to the sorbent and insufficient amount of desorption gas to quantitatively move all analytes from the sorbent to the analytical device. In FIG. 9, there is shown a schematic side view of a preferred desorption process in which the trapped compounds are desorbed thermally into the gas chromatograph 80 using a carrier gas diverted to the micro cartridge with a help of a valve 82. Flow controller 90 supplies a well defined flowrate of a carrier gas to valve 82 via tubing 94 which in turn delivers the carrier gas either to the injection port 96 via tubing 92 or to micro cartridge 2 via tubing 86. The micro cartridge 2 is connected to the tubing 86 containing receptacle 88 in a similar way to syringe shown in FIG. 8 with a help of nut 74 and ferrule 78. After the micro cartridge is placed in the liner of the injection port 96 of the gas chomatograph 92, the gas is diverting from flowing directly to the injector via tubing 92 to flowing through tubing 86 and micro cartridge to the liner located in the injection port. The carrier gas removes the analytes from the sorbent into the gas chromatograph. The thermal desorption can be simplified if the structure of the sorbent in the micro cartridge consists of layers of different sorbing characteristics divided into segments (as shown in FIG. 1) by locating the weakest sorbent close to the entrance passage 14 and the strongest sorbent deepest into the cartridge 2 near the closure 12. In this arrangement, the middle sorbent is preferably of medium effectiveness. This will result in the analytes that are the most difficult to adsorb, being adsorbed on the third sorbent from the entrance, the analytes of medium difficulty will be adsorbed on the second sorbent from the entrance and the easiest analytes to adsorb will be adsorbed on the first sorbent from the entrance. The analytes are then adsorbed throughout the three segments. If the strongest adsorbing sorbent is located nearest the entrance or if only one strong sorbent is used, the sorbent will adsorb strongly binding analytes so well that it would be difficult to desorb analytes from the cartridge.

Figure 10:
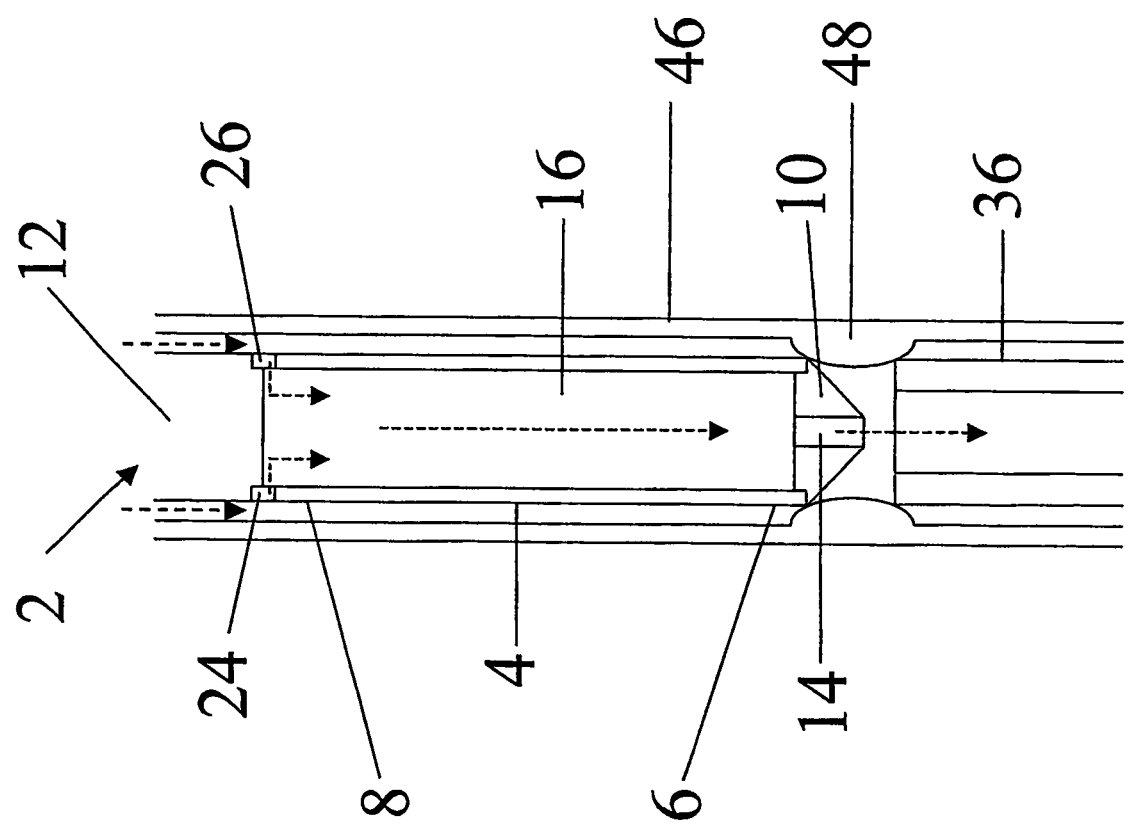
FIG. 10 is a side view of a liner that is used to divert the flow of gas during introduction of the micro cartridge.

FIG. 10 illustrates the preferred desorption approach, which does not require a valve, but rather uses a liner 46 containing a restriction 48 to divert the carrier gas flow through the cartridge, when the micro cartridge 2 is introduced through the septa (not shown) into the liner. There is shown a schematic side view of the cartridge 2 located in the liner 46. The restriction of the liner seals the cartridge 2, which facilitates the diversion of flow of gas through the sorbent 16 by closure of the gas path to a column 36 during the introduction of the cartridge 2 into the injection port The carrier gas is forced to enter the micro cartridge through the openings 24 and 26 pass through the sorbent 16 and effectively transfers the analytes into column 36 which is also sealed by the restriction producing very low dead volume. The carrier gas flow direction is indicated by broken arrows. Analyte transfer to analytical instruments for separation and quantification can be also facilitated with liquid desorption (using solvents or water). Liquid desorption can be accelerated by using a high temperature. The system can be designed to perform sampling and desorption directly in the field using on-site instrumentation.

Figure 11:
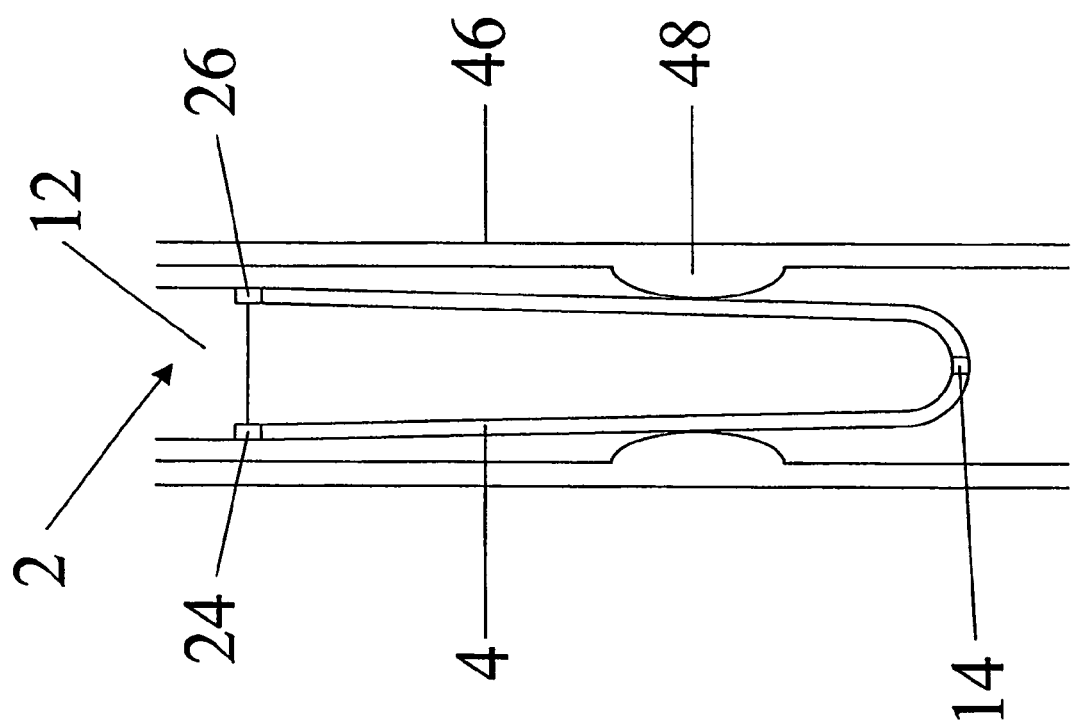
FIG. 11 is a schematic side view of the micro cartridge located within an injection port.

As FIG. 11 illustrates, a further embodiment of micro cartridge 2 has a tapered tubular member 4, which would also facilitate sealing in the liner 46 with restriction 48. This embodiment does not contain the closure 10 but rather the tubular member 4 has a domed end with a small opening 14 in the center. Alternatively micro cartridge 2 could have tiny side openings (not shown) in place of the center opening 14 or it could have tiny openings in the cartridge tip or free end if sorbent is bonded to the inner surface of the tubular member 4 of a micro cartridge 2 (also not shown). The tiny openings must be much smaller compared to the inside diameter of the needle to prevent the loss of sorbent.

Figure 14:
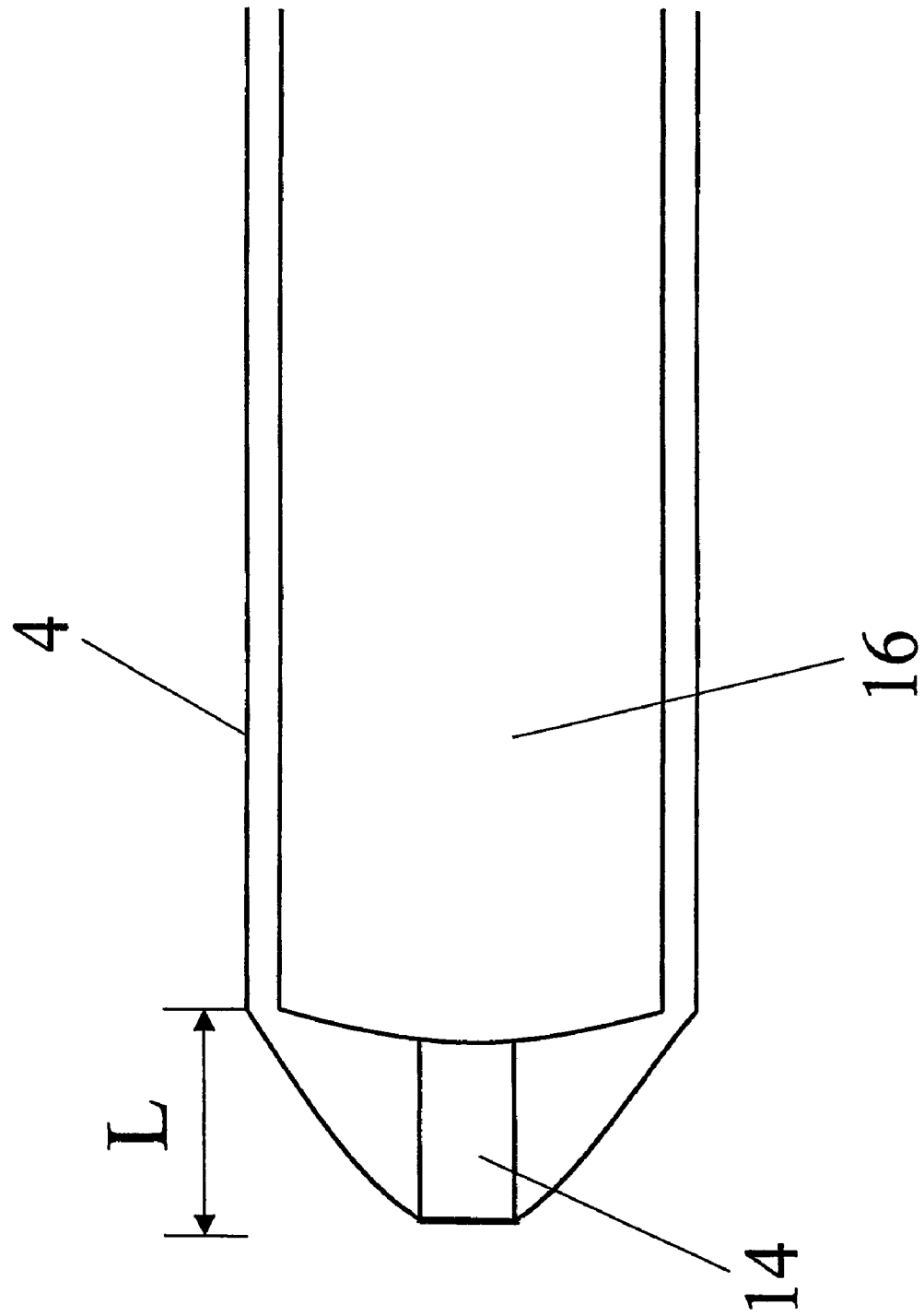
FIG. 14 is a schematic side view of part of a needle used for passive sampling.
Figure 15:
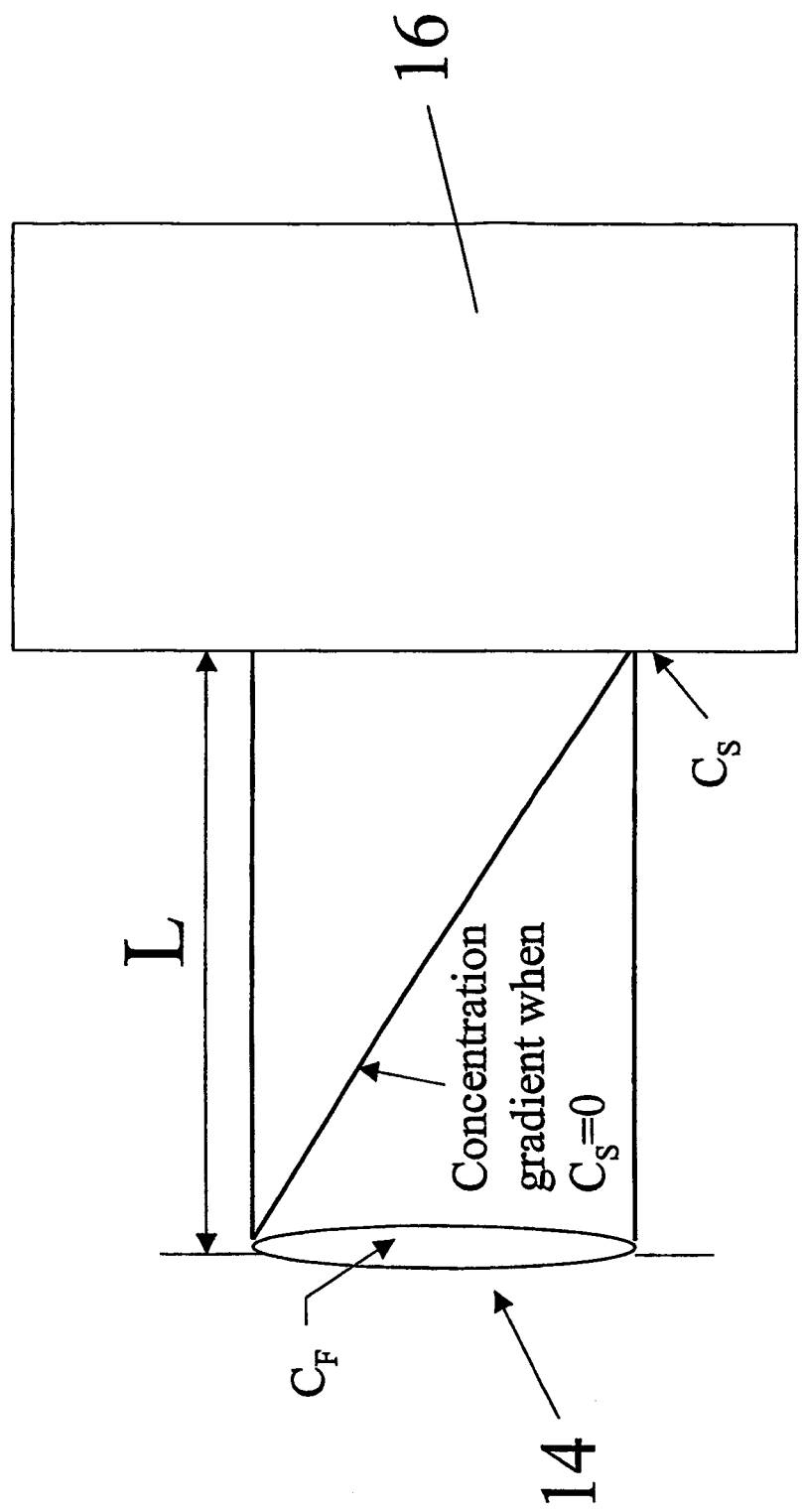
FIG. 15 is a schematic view of a passive sampler.

The needle trap can also be used as passive sampler when the needle is exposed to the sample directly allowing components of the sample to diffuse into the needle (FIGS. 14, 15 and Table 3). To extend the integration time, the diffusion path can be made longer by placing the micro cartridge inside a holder, which has small opening 40 as illustrated on FIG. 4. This results in independence of the sampling rate from the sample matrix convection conditions (see FIG. 17). The adsorbed compounds can be desorbed thermally into the analytical instrument with the help of flowing gas. The thermal desorption is simplified if the structure of the sorbent consist of layers of different sorbing characteristics, such as the weakest sorbent is close to the exit and the strongest deepest in the cartridge (see FIG. 1).

TABLE 3

Passive Time Weighted Average Sampling (TWA) with MCD

| Extraction 1 time | Mass (ng) Extracted | | | |
|---|---|---|---|---|
| | Octane | Nonane | Decane | Undecane |
| 30 min | 0.53 | 0.70 | 0.47 | 0.67 |
| 1 hr | 1.05 | 1.14 | 0.74 | 1.13 |

Theory of Passive Time Weighted Average (TWA) Sampling with a Micro Cartridge Device (MCD).

FIG. 15 depicts a MCD passive sampler, which consists of a sorbent positioned a distance L from an opening of fixed cross-sectional area A opening 14. The important properties of the passive sampler are its physical dimensions and the efficiency of the sorbent.

The basic process of analyte uptake by the MCD passive sampler can be described by Fick's first law of diffusion (eq 2)

$$J = -D\left(\frac{dc}{dL}\right) \quad (2)$$

where D is the analyte diffusion coefficient (cm$^2$ min$^{-1}$), dc/dL is the analyte concentration gradient from the opening of the sampler to the surface of the sorbent, and J, which is defined as $$\frac{dn}{Adt},$$

describes the flux of the analyte:

$$\frac{dn}{Adt} = -D\frac{dc}{dL} \quad (3)$$

where dn is the amount of analyte passing through a cross-sectional area A during a sampling period dt. dn is proportional to the linear concentration gradient in the sampler (dc/dL) and the analyte diffusion coefficient D. For a given sampler, both cross sectional area A and diffusion path length L are constant When sampling reaches the. steady state:

$$\frac{dc}{dL} = \frac{\Delta C}{L} = \frac{C_{sorbent} - C_{face}}{L} \quad (4)$$

If the sorbent has a large capacity and strong affinity for target analytes, i.e. acts as a zero sink, $C_{sorbent}$, the concentration of analyte at the sorbent/gas interface, is negligible. In these circumstances, eq 4 reduces to:

$$\frac{dc}{dL} = \frac{-C_{face}}{L} \quad (5)$$

If $C_{face}$, the analyte concentration at the opening, is equal to $C_{bulk}$ (the bulk analyte concentration), which is true when the sampled matrix is well agitated, then:

$$\frac{dc}{dL} = \frac{-C_{bulk}}{L} \quad (6)$$

substituting eq 6 into eq 3, we obtain, after rearrangement:

$$dn = \frac{AD}{L}C_{bulk}dt \quad (7)$$

Because the dimensions of the expression $$\frac{AD}{L}$$

are cm³ min⁻¹, it is defined as the formal sampling rate $S_R$:

$$S_R = \frac{AD}{L} \quad (8)$$

This definition indicates that sampling rate, $S_R$, is proportional to the cross-sectional area, A, and the analyte diffusion coefficient, D, and inversely proportional to the diffusion path length, L. Combing eqs 7 and 8 yields eq 9:

$$dn = S_R C_{bulk} dt \quad (9)$$

and after integration of both sides over time, eq 9 reduces to:

$$n = S_R \int_1^2 C_{bulk} dt \quad (10)$$

which describes the passive sampler response to a transient concentration of an analyte as a function of time. For a constant analyte concentration, eq 10 reduces to:

$$n = S_R C_{bulk} t \text{ or} \quad (11)$$

$$S_R = \frac{n}{C_{bulk} t} \quad (12)$$

Equation 11 indicates that the rate of uptake of analyte mass by the passive sampler (n/t) is directly proportional the sampling rate of the sampler $S_R$ and the bulk analyte concentration.

According to eq 8, the sampling rate, $S_R$, will be a constant for a given analyte and passive sampler, and can be determined theoretically. Sometimes, however, it is difficult to determine $S_R$ theoretically, especially when the diffusion coefficient is not available. In these circumstances eq 12 indicates that an empirical approach can be used—the mass loading, n, is determined during a sampling period, t, at a constant concentration $C_{bulk}$. When $S_R$ is determined, it can be used to quantify unknown analyte concentrations by use of eq 13

$$C_{bulk} = \frac{n}{S_R t} \quad (13)$$

It is in this way that the micro cartridge can be used practically as a passive sampler.

Standard Gas Generator n-Pentane, n-hexane, n-heptane, n-octane, n-nonane, n-decane, n-undecane, carbon disulfide, and toluene were purchased from Sigma-Aldrich (Mississauga, ON, USA). ORBO™-32 tubes, gas purifiers, Teflon™ tubing, syringes, Thermogreen™ septa, gas sampling bulbs, and vials were purchased from Supelco (Mississauga, ON, USA). The timer was purchased from VWR (Mississauga, ON, USA). Ultra-high-purity hydrogen, nitrogen, and helium were purchased from Praxair (Waterloo, ON, USA). Personal air pumps and the mini-Buck calibrator were purchased from A. P. Buck (Orlando, Fla., USA). Ultra-pure air for the standard gas generator and for flame ionization detection was supplied by a Whatman zero air generator (model 76-803).

National Institute of Standards and Technology (NIST) traceable certified permeation tubes (Kin-Tech Laboratories, La Marque, Tex., USA) were used for generation n-alkanes. Ultra-high-purity air at 50 psig was supplied by use of thoroughly cleaned copper tubing and Swagelok™ connectors. The supplied air was also scrubbed by use of a Supelpure HC hydrocarbon trap before entering the standard gas generator. All permeation tubes were placed inside a glass permeation cylinder (KIN-Tech Laboratories, La Marque, Tex., USA) and swept with a constant flow of dilution air. The actual air flow rate was verified by use of a primary gas flow standard Mimi-Buck calibrator (A. P. Buck, Orlando, Fla., USA). A wide range of concentrations of n-alkanes was obtained by adjusting both air-flow rates and permeation cylinder temperature.

Sampling Chamber

Sampling-chamber temperature was maintained at 25±0.3° C. To investigate the effect of face velocity, a multi-chamber with three different diameters was installed downstream from the main sampling chamber. The standard gas generator and sampling chambers were validated by use of ORBO™ adsorbent tubes combined with A. P. Buck I. H. personal air pumps for conventional NIOSH methods.

Discussion of the Results.

For the exhaustive extraction (see FIG. 12) the concentration of analyte C can be calculated using the equation 1:

$$C = \frac{M}{V} \quad (14)$$

where M is the mass extracted and V is volume of the sample. Therefore using data from Table 1 we can estimated the concentration of analytes in the standard gas to be about 0.15 ng/ml for Octane, 0.61 ng/ml for Nonane, 0.49 ng/ml for Decane and 0.67 ng/ml for Undecane.

1. For equilibrium extraction (see FIG. 13) from large sample volume, the mass extracted can be expressed as:

$$M = KV_e C \quad (15)$$

where the $V_e$ is the volume of the absorbing sorbent (in our experiment we used poly(dimethylsiloxane)-PDMS) and K is the sorbent-matrix distribution constant. The data from the Table 2 indicate that there is an advantage in using equilibrium methods rather then exhaustive extraction methods since more analytes are extracted for samples larger then breakthrough volumes. However, the quantitation is more involved, specially for complex samples since the K needs to be precisely defined. Using the data from Tables it is possible to find out that the ratio of K for decane and undecane is about 2, which corresponds to literature value (J. Pawliszyn, Solid Phase Microextraction, Wiley, N.Y. 1997).

Figure 16:
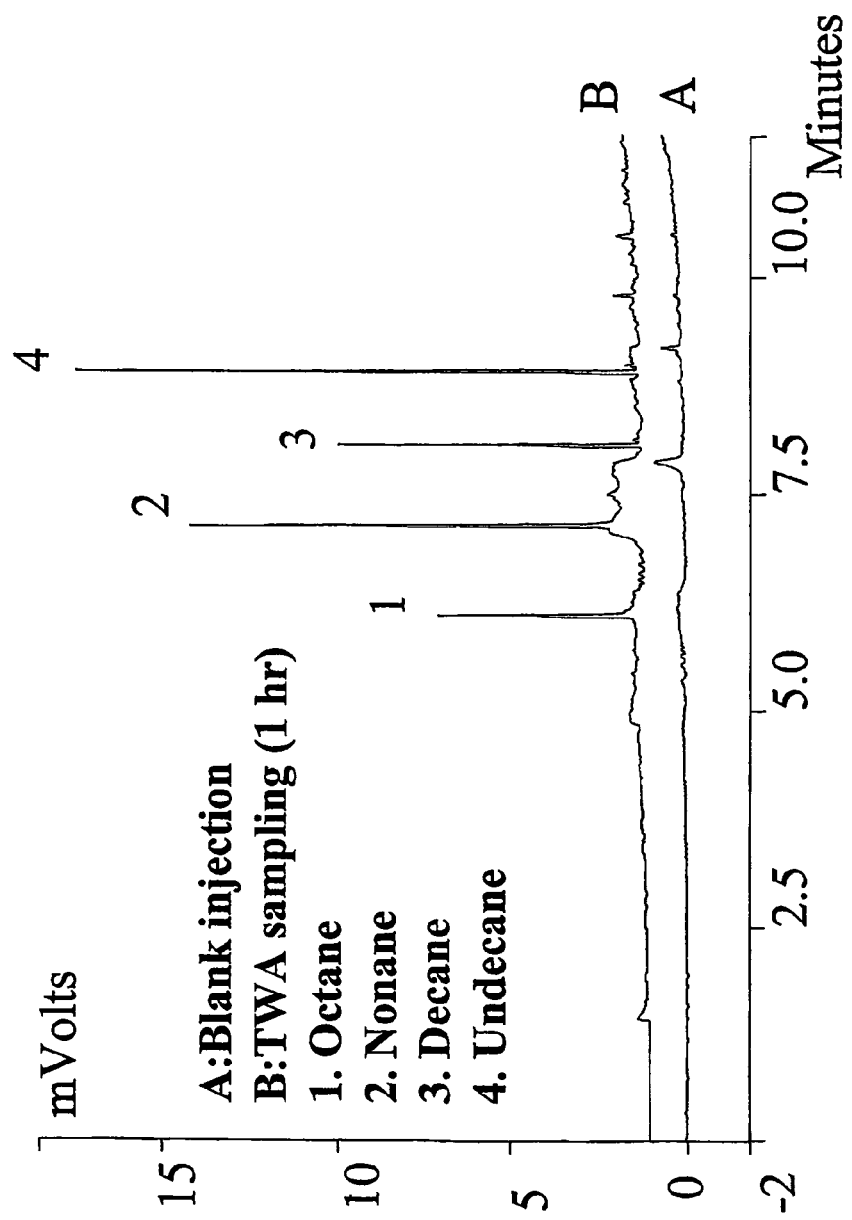
FIG. 16 is a graph of passive sampling results.

2. For time-weighted average sampling (see FIG. 16) the amount of accumulated compound on the sorbent as a function of time can be expressed as:

$$M = \frac{AD}{Z} \int C dt \quad (16)$$

where A is the surface area opening of the side-hole and D is the diffusion coefficient of the analyte in the matrix. Table 3 shows that the amount of analytes diffused and trapped onto the sorbent is proportional to time as the amount of extracted analytes is doubled by extending exposure from 30 minutes to 1 hour. The above examples clearly demonstrate that a single micro cartridge can perform all three modes of extraction.

The important condition for proper operation of the TWA sampler is that bulk analyte concentration, $C_{bulk}$ must equal the analyte concentration at the face of the opening, $C_{face}$, i.e., $C_{bulk} = C_{face}$. A passive sampler can be expected to sample accurately if, essentially, all resistance to analyte transport is contained within the stagnant air layer inside the device. As the velocity of air across the sampler surface (face velocity) decreases external resistance to mass transfer associated with convection increases. When this latter resistance becomes a significant fraction of the internal diffusional resistance the mass of analyte collected will become less than that predicted on the basis of Fick's first law of diffusion. This suggests that a minimum air velocity is required and that when this minimum is achieved performance will be velocity-insensitive over a wide range. For a typical passive sampler, a large surface area is required to ensure a large amount of analyte is sampled, to satisfy analytical detection limits. A large surface area, in turn, requires a large face velocity, usually 15 to 50 ft min$^{-1}$, to ensure that $C_{bulk}$ is equal to $C_{face}$.

Figure 17:
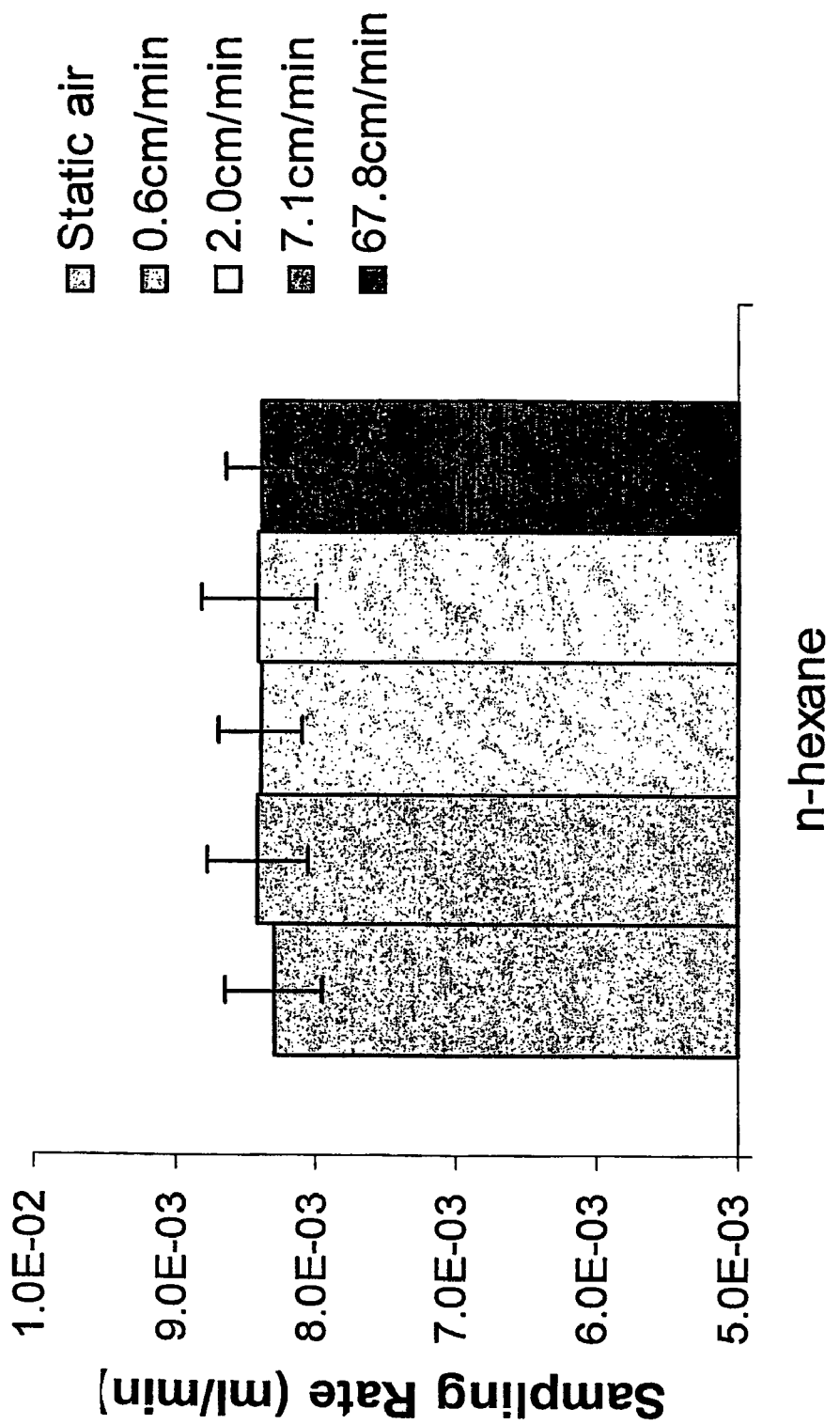
FIG. 17 is a graph of the adsorption rate for n-hexane under varying air flow conditions.

Micro Cartridge Device (MCD) takes advantage of thermal desorption, which transfers all the collected analytes into the instruments used for quantification, thus enhancing analytical sensitivity. A MCD sampler, for which the cross-sectional area of the opening is very small, requires a very small face velocity only. Experimental assessment of velocity-dependence indicated there were no significant effects of using the sorbent system with small diffusion orifice at a face velocity as low as 0.6 cm min$^{-1}$ (FIG. 17). This is a significant advantage of the MCD device over other passive samplers and means that, in practice, the micro cartridge device can be used for TWA passive sampling without considering the face velocity problem, which must be taken seriously when deploying other passive samplers.

The components of the sample can be both chemical compounds as well as particulate matter present in the sample. Fractionation is also possible during the desorption in a manner similar to how it is presently performed in solid phase extraction (SPE). Different solvents and/or temperatures can be used to separate interferences from target analytes.

Preferably, the passages in the cartridge of a size that is substantially smaller than a cross section of the cartridge. Though not essential, it is also preferable that there are means to cool the cartridge when there is access between the fluid and the sorbent and there are means to heat the cartridge during desorption. While the micro cartridge is described as being used to sample and extract components of interest from a fluid, the fluid would most often be air. The sorbent can consist of small size particulate material or highly porous monolithic sorbent prepared by polymerization of appropriate monomers directly in the micro cartridge. The monolithic sorbent can be derived from a sol-gel process. The sorbent can be bound to the inner surface of the micro cartridge. The sorbent can also have a reagent which selectively reacts with components of interest.

The analysis instrument can be a capillary gas chromatograph where the fluid is a gas or a liquid chromatographic instrument where the fluid is a liquid. A capillary electrophoresis instrument is also suitable. In addition, the analysis instrument can be a micro machined instrument.

The passage where the fluid to be sampled enters the micro cartridge is an inlet Preferably, the micro cartridge has an outside diameter that is substantially less than two millimeters and, still more preferably, the cartridge has an outside diameter that is substantially less than 1 millimeter.

The housing can be completely sealed when it encloses the micro cartridge or it can have one or more openings that correspond to passages in the micro cartridge. The openings can have plugs in them to seal the openings.

I claim:

1. A method of using a device for sampling and extracting components of interest from fluid, the device having an elongated micro cartridge containing a sorbent and having passages therein, to permit access between said fluid and said sorbent, wherein there is a housing into which said micro cartridge can be removably placed, said housing having an opening therein corresponding to a passage in said cartridge, said opening having a removable seal and a substantially small diameter compared to a length of said opening, said micro cartridge being sized and shaped to fit into an injection port of an analysis instrument where the components of interest can be desorbed, said method comprising exposing the micro cartridge and sorbent to a fluid, inserting said cartridge into an injection port of the suitable analysis instrument and desorbing the components of interest from said cartridge, said method further including the steps of placing the cartridge in said housing, sealing said housing and sealing said opening with a plug, removing said plug immediately before sampling, carrying out sampling by diffusion while said cartridge is in said housing, replacing said plug in said opening when sampling has been completed, transporting the housing and cartridge to the analysis instrument, removing the cartridge from the housing, placing the cartridge into an injection port of the analysis instrument and carrying out desorption;

wherein the injection port has a liner and desorption is carried out directly from said cartridge to said liner, said liner containing a restriction sealing said cartridge during desorption to prevent desorption fluid from entering said cartridge through the passage used for sampling and permit desorption fluid to enter said cartridge through another passage in said cartridge so that desorption fluid flows through the sorbent and then out through the passage used for sampling;

wherein the sorbents are arranged in segments, wherein a weakest sorption segment of the sorbent is located closest to an inlet, a strongest sorption segment is located further from said inlet, and an intermediate sorption segment is located between the weakest and the strongest segments.

2. A method as claimed in claim 1, wherein said cartridge is connected to the injection port of the analytical instrument so that fluid can flow through said cartridge into said port to assist in desorption.

3. A method as claimed in claim 1 including the steps of using the cartridge for sampling off site, inserting the cartridge into a sealed housing after completing said sampling, transporting the housing to the analysis instrument and removing the cartridge from the housing.

4. A method as claimed in claim 3, wherein said analytical instrument is automated, said method including the steps of automatically removing a micro cartridge from said cartridge holder and placing said micro cartridge into the injection port of the analytical instrument and automatically carrying out desorption.

5. A device for sampling or extracting a component of interest from a fluid, said device comprising an elongated micro cartridge, said cartridge containing a sorbent and having passages therein to permit access between said fluid and said sorbent, wherein there is a housing into which said device can be removably placed, said housing having an opening corresponding to a passage in said cartridge to enable sampling by diffusion through said cartridge while said cartridge remains in said housing, said opening having a removable seal and a diameter substantially small compared to a length of the opening, said micro cartridge being sized and shaped to fit into an injection port of an analysis instrument where said component of interest can be desorbed;

wherein the injection port has a liner and desorption is carried out directly from said cartridge to said liner, said liner containing a restriction sealing cartridge during desorption to prevent desorption fluid from entering said cartridge through the passage used for sampling and permit desorption fluid to enter said cartridge through another passage in said cartridge so that desorption fluid flows through the sorbent and then out through the passage used for sampling;

wherein the sorbents are arranged in segments wherein a weakest sorption segment of the sorbent is located closest to an inlet, a strongest sorption segment is located further from said inlet, and an intermediate sorption segment is located between the weakest and the strongest segments.

6. The device according to claim 5, wherein said cartridge is connected to an injection port of the analytical instrument so that fluid can flow through said cartridge into said port to assist in desorption.

7. The device according to claim 5, wherein the sorbent has a reagent that selectively reacts with the components of interest.

8. The device of claim 5, wherein there are means to heat said cartridge during desorption.

9. A device as claimed in claim 5, wherein the cartridge is sized and shaped to fit within a cartridge carousel of said analysis instrument, said analysis instrument being automated, said carousel having at least one cartridge receptor therein, said passages being sealed when said cartridge is located in the receptor.

10. An apparatus comprising a device as claimed in claim 5, wherein the apparatus has a housing into which said device can be inserted and removed, said housing having an opening corresponding to a passage in said cartridge to enable sampling through said cartridge while said cartridge remains within said housing by diffusion, said opening having a removable seal and a diameter substantially smaller than a length of the opening.

11. An apparatus comprising a device as claimed in claim 5, wherein the sorbent is present across a cross-section of the microcartridge.

12. A device as claimed in claim 5, wherein the cartridge is sized and shaped to fit within a cartridge carousel of said analysis instrument, said analysis instrument being automated, said carousel having at least one cartridge receptor therein, said passages being sealed when said cartridge is located in the receptor.

13. A device as claimed in claim 5, wherein the passages comprise a side passage in the side of the cartridge for use during desorption which is sealed during sampling to allow sampling from other of said passages further from an inlet end.

14. A device for sampling or extracting a component of interest from a fluid, said device comprising an elongated micro cartridge, said cartridge containing a sorbent and having passages therein to permit access between said fluid and said sorbent, wherein there is a housing into which said device can be removably placed, said housing having an opening corresponding to a passage in said cartridge to enable sampling through said cartridge while said cartridge remains in said housing, said opening having a removable seal and a diameter substantially small compared to a length of the opening, said micro cartridge being sized and shaped to fit into an injection port of an analysis instrument where said component of interest can be desorbed;

wherein the injection port has a liner and desorption is carried out directly from said cartridge to said liner, said liner containing a restriction sealing said cartridge during desorption to prevent desorption fluid from entering said cartridge through the passage used for sampling and permit desorption fluid to enter said cartridge through another passage in said cartridge so that desorption fluid flows through the sorbent and then out through the passage used for sampling;

wherein the sorbents are arranged in segments wherein a weakest sorption segment of the sorbent is located closest to an inlet, a strongest sorption segment is located further from said inlet, and an intermediate sorption segment is located between the weakest and the strongest segments.

15. The device according to claim 14, wherein said cartridge is connected to an injection port of the analytical instrument so that fluid can flow through said cartridge into said port to assist in desorption.

16. The device according to claim 14, wherein the sorbent has a reagent that selectively reacts with the components of interest.

17. The device of claim 14, wherein there are means to heat said cartridge during desorption.

18. The device of claim 14, wherein the sorbent is present across a cross-section of the microcartridge.

19. An apparatus comprising a device as claimed in claim 14, wherein the apparatus has a housing into which said device can be inserted and removed, said housing having an opening corresponding to a passage in said cartridge to enable sampling through said cartridge while said cartridge remains within said housing by diffusion, said opening having a removable seal and a diameter substantially smaller than a length of the opening.

20. A device as claimed in claim 14, wherein the sorbent is present across a cross-section of the microcartridge.

\* \* \* \* \*